US008173388B2

(12) United States Patent
Pasmore et al.

(10) Patent No.: US 8,173,388 B2
(45) Date of Patent: May 8, 2012

(54) SELF-CONTAINED BIOLOGICAL INDICATOR

(75) Inventors: Mark Edward Pasmore, Greyslake, IL (US); Phillip P. Franciskovich, Concord, OH (US); Tricia A. Cregger, Fairlawn, OH (US); Alan M. Solomon, Buffalo Grove, IL (US)

(73) Assignee: American Sterilizer Company, Mentor, OH (US)

( * ) Notice: Subject to any disclaimer, the term of this patent is extended or adjusted under 35 U.S.C. 154(b) by 805 days.

(21) Appl. No.: 12/241,473

(22) Filed: Sep. 30, 2008

(65) Prior Publication Data

US 2010/0081165 A1    Apr. 1, 2010

(51) Int. Cl.
*C12Q 1/22* (2006.01)
(52) U.S. Cl. .............. 435/31; 435/287.4; 435/4
(58) Field of Classification Search ............ 435/31
See application file for complete search history.

(56) References Cited

U.S. PATENT DOCUMENTS

| | | | |
|---|---|---|---|
| 2,854,384 A | 9/1958 | Beakley et al. ............... 195/54 |
| 2,959,889 A | 11/1960 | Gausewitz ..................... 46/41 |
| 3,213,902 A | 10/1965 | Mote ............................ 141/18 |
| 3,239,429 A | 3/1966 | Menolasino et al. ......... 195/54 |
| 3,346,464 A | 10/1967 | Ernst ............................ 195/54 |
| 3,378,168 A | 4/1968 | Hildebrandt ................. 222/83 |
| 3,440,144 A | 4/1969 | Andersen ................... 195/103.5 |
| 3,551,295 A | 12/1970 | Dyer .......................... 195/103.5 |
| 3,585,112 A | 6/1971 | Ernst .......................... 195/103.5 |
| 3,616,263 A | 10/1971 | Anandam ................... 195/127 |
| 3,661,717 A | 5/1972 | Nelson ....................... 195/103.5 |
| 3,752,743 A | 8/1973 | Henshilwood .............. 195/127 |
| 3,796,635 A | 3/1974 | Delente ....................... 195/65 |
| 3,846,242 A | 11/1974 | Ernst .......................... 195/103.5 |
| 4,011,139 A | 3/1977 | Horwath et al. ............. 195/65 |
| 4,162,942 A | 7/1979 | Gunther ....................... 435/17 |
| 4,284,719 A | 8/1981 | Agerhem et al. ............. 435/18 |
| 4,291,122 A | 9/1981 | Orelski ........................ 435/31 |
| 4,304,869 A | 12/1981 | Dyke ........................... 435/296 |
| 4,348,209 A | 9/1982 | Murtaugh et al. ........... 23/232 |
| 4,416,984 A | 11/1983 | Wheeler, Jr. ................ 435/31 |
| 4,448,548 A | 5/1984 | Foley ........................... 374/160 |
| 4,461,837 A | 7/1984 | Karle et al. .................. 435/296 |
| 4,528,268 A | 7/1985 | Andersen et al. ............ 435/31 |
| 4,579,823 A | 4/1986 | Ryder .......................... 435/296 |
| 4,580,682 A | 4/1986 | Gorski et al. ................ 206/569 |
| 4,591,554 A | 5/1986 | Koumura et al. ............ 435/18 |
| 4,596,773 A | 6/1986 | Wheeler, Jr. ................ 435/31 |
| 4,603,108 A | 7/1986 | Bascomb ..................... 435/34 |
| 4,723,691 A | 2/1988 | Minkevitch et al. ........ 222/210 |
| 4,741,437 A | 5/1988 | Gorski et al. ............... 206/222 |
| 4,743,537 A | 5/1988 | McCormick et al. ....... 435/296 |
| 4,839,291 A | 6/1989 | Welsh et al. ................. 435/296 |
| 4,883,641 A | 11/1989 | Wicks et al. ................. 422/50 |
| 4,885,253 A | 12/1989 | Kralovic ..................... 435/296 |
| 5,022,411 A | 6/1991 | Guirguis ...................... 128/771 |
| 5,038,793 A | 8/1991 | Guirguis ...................... 128/760 |
| 5,073,488 A | 12/1991 | Matner et al. ................ 435/31 |
| 5,079,144 A | 1/1992 | Carr et al. .................... 435/32 |
| 5,223,401 A | 6/1993 | Foltz et al. ................... 435/18 |
| 5,252,484 A | 10/1993 | Matner et al. .............. 435/288 |
| 5,366,872 A | 11/1994 | Hird et al. .................... 435/31 |
| 5,405,580 A | 4/1995 | Palmer ........................ 422/28 |
| 5,418,167 A | 5/1995 | Matner et al. .............. 435/288 |
| 5,486,459 A | 1/1996 | Burnham et al. ............ 435/31 |
| 5,516,648 A | 5/1996 | Malchesky et al. ......... 435/31 |
| 5,736,355 A | 4/1998 | Dyke et al. ................... 435/31 |
| 5,739,004 A | 4/1998 | Woodson ...................... 435/31 |
| 5,770,393 A | 6/1998 | Dalmasso et al. ........... 435/31 |
| 5,830,683 A | 11/1998 | Hendricks et al. ........... 435/31 |
| 5,866,356 A | 2/1999 | Albert et al. ................. 435/31 |
| 5,870,885 A | 2/1999 | Biddle et al. ................. 53/436 |
| 5,955,296 A | 9/1999 | Roll ............................. 435/31 |
| 5,989,852 A | 11/1999 | Hendricks et al. ........... 435/31 |
| 6,025,189 A | 2/2000 | Bolea et al. ................ 435/287.4 |
| 6,063,591 A | 5/2000 | Bolea .......................... 435/31 |
| 6,121,012 A | 9/2000 | Falkowski et al. ........... 435/39 |
| 6,355,448 B1 | 3/2002 | Foltz et al. ................... 435/31 |
| 6,528,277 B1 | 3/2003 | Hendricks et al. ........... 435/31 |
| 6,566,090 B2 | 5/2003 | Witcher et al. .............. 435/31 |
| 6,623,955 B2 | 9/2003 | Matner et al. .............. 435/287.4 |
| 6,924,139 B2 | 8/2005 | Eveland et al. ............ 435/287.4 |
| 6,942,989 B2 | 9/2005 | Felkner et al. .............. 435/31 |
| 7,100,646 B2 | 9/2006 | Py et al. ...................... 141/329 |
| 7,116,930 B2 | 10/2006 | Wegman et al. ............ 399/262 |
| 2002/0058296 A1 | 5/2002 | Miller et al. ................. 435/31 |
| 2003/0064507 A1 | 4/2003 | Gallagher et al. ......... 435/287.2 |
| 2004/0248235 A1 | 12/2004 | Foltz et al. ................... 435/31 |
| 2007/0092969 A1 | 4/2007 | Song et al. .................... 436/1 |

FOREIGN PATENT DOCUMENTS

| | | |
|---|---|---|
| EP | 0000063 A1 | 12/1978 |
| GB | 1547747 A | 6/1979 |
| GB | 2128204 A | 4/1984 |
| GB | 2186974 A | 8/1987 |
| WO | 8605206 A1 | 9/1986 |

OTHER PUBLICATIONS

International Search Report and Written Opinion, Application No. PCT/US2009/055822, mailed Apr. 6, 2010. International Preliminary Report on Patentability; Application No. PCT/US2009/055822, issued Apr. 5, 2011.

*Primary Examiner* — Jon P Weber
*Assistant Examiner* — Tiffany Gough
(74) *Attorney, Agent, or Firm* — Renner, Otto, Boisselle & Sklar, LLP

(57) ABSTRACT

The disclosed invention provides a self-contained sterilization indicator for evaluating the effectiveness of a sterilization process. The sterilization indicator includes a cap configured for housing a growth medium, the cap being mountable on a container that contains a concentration of microorganisms. The cap comprises an inner chamber for housing the growth media. The inner chamber has an opening and a breakable barrier overlying the opening for encapsulating the growth media within the inner chamber of the cap. The biological indicator is adapted for breaking the breakable barrier at a selected time to introduce the growth medium into the container such that the growth medium contacts the microorganisms.

38 Claims, 6 Drawing Sheets

SELF-CONTAINED BIOLOGICAL INDICATOR

TECHNICAL FIELD

The present invention relates to sterilization indicators, e.g., self-contained biological indicators, for evaluating the efficiency of a sterilization process and to methods of evaluating the efficiency of a sterilization process using such indicators.

BACKGROUND

Sterilization processes are utilized to sterilize a wide variety of materials including, for example, medical instruments, surgical instruments, and the like. Items to be sterilized are typically placed in a chamber and subjected to conditions believed to be sufficient to effectively sterilize the items and render them free (or at least to a pre-determined, acceptable level) of biological contaminants. There are a variety of sterilization techniques by which sterilization can be effected including steam sterilization, exposure to gaseous sterilants (e.g., ethylene oxide, vaporized hydrogen peroxide, and the like), plasma sterilization, and the like. Regardless of the techniques utilized to sterilize items, evaluating the effectiveness of the applied sterilization process is beneficial to ensure that the process provided the desired degree of sterilization. Evaluating the effectiveness of a process may be particularly desirable when sterilizing items such as medical instruments and devices invasive to the human body.

The efficacy of sterilization processes are evaluated using sterilization indicators, which typically evaluate whether a sterilization resistant challenge material survives a sterilization process. A typical biological indicator system, for example, includes a source of microorganisms (e.g., bacterial spores), a culture medium, and a visible detector to indicate the presence or absence of viable microorganisms. The indicator system is subjected to a sterilization cycle, which should be sufficient to kill the microorganisms. Following the sterilization cycle, the source of microorganisms is combined with the culture medium and then incubated to encourage the outgrowth of any remaining viable microorganisms. During the incubation period, the indicator system is evaluated to determine whether any microorganisms survived the sterilization process. The indicator may be evaluated visually (e.g., by turbidity or a color change) or with a detector (e.g., by spectroscopy using a spectrophotometer, fluorometer, or the like), to measure a selected property such as pH change, fluorescence, change in light absorbance, and the like.

Commercially used biological indicators frequently employ a system in which the culture medium is separated from microorganisms by placing the growth medium in a glass ampoule and disposing the ampoule within a container housing the microorganisms. Following the sterilization process, the biological indicator is activated by breaking the ampoule, which releases the growth medium into the container.

Commercially used biological indicators may also have relatively long incubation periods to obtain a detectable level of spore outgrowth. For example, commercially used biological indicators may require incubation periods from eighteen hours to up to seven days. Depending on the items being sterilized, such long periods for evaluating the efficacy of a sterilization process may not always be practical. In particular, medical devices and instruments that have been sterilized should not be used while still evaluating the efficacy of the sterilization process to which the devices were subjected. But it is costly to have medical devices inactive for extended periods while determining if they have been sufficiently sterilized.

To provide a more rapid indicator to evaluate sterilization efficacy, some systems evaluate the activity of enzymes occurring in microorganisms rather than microorganism growth. For example, 3M Corporation makes a rapid readout indicator under the tradename ATTEST®, which utilizes an enzyme that occurs naturally in the spore coat to degrade 4-methylumbelliferyl-$\alpha$-D-glucoside to a fluorescent breakdown product. The fluorescence signal associated with this enzyme can be measured within one to three hours. In this indicator, a non-fluorescent substrate is added to the media, the substrate degrades to produce a fluorescent compound, and the fluorescent compound, rather than microorganism outgrowth, is monitored to evaluate the process. These indicators are utilized for evaluating steam sterilization processes. During sterilization, the steam heat inactivates the enzyme that performs the non-fluorescent to fluorescent reaction.

Other examples of biological indicators that employ enzymes whose activity is correlated with spore viability to give an indication of sterilization efficacy include those described in U.S. Pat. Nos. 5,073,488; 5,223,401; 5,418,167; 5,866,356, and 6,566,090.

SUMMARY

The present invention provides a self-contained sterilization indicator for evaluating a sterilization process, the indicator comprising a cap for housing a growth medium and/or a substrate reactive with an enzyme that is mountable on a container for housing microorganisms and/or an enzyme. In one aspect, the present invention provides a self-contained biological indicator for determining the effectiveness of a sterilization process, the biological indicator comprising: a polymeric container for holding a concentration of microorganisms and/or an enzyme, the container having an upper end, a lower end, and an opening at the upper end; and a cap formed from a polymeric material, the cap having an outer wall, an upper, closed end, a lower end, an opening adjacent the lower end of the cap, and an inner wall defining an inner chamber having an opening adjacent the lower end of the cap, the inner chamber being suitable for holding a growth medium and/or a substrate reactive with an enzyme, the cap comprising a breakable barrier overlying and covering the opening of the inner chamber.

A problem with sterilization indicators that use glass ampoules to store the growth medium is that the ampoule must be broken to activate the indicator. The ampoule is typically located within the container portion of the indicator. When the ampoule is shattered, fragments from the ampoule may obstruct the light path when the indicator is in a reader to be analyzed. Applicants have found that by encapsulating the growth medium in the cap with a breakable barrier formed from a polymeric material and/or foil material, which do not shatter upon breaking, the possibility of light path obstruction in the container is greatly reduced or even eliminated.

The geometry of the container serves as the light path. By placing the microorganisms in the container and the growth medium in the cap, Applicants have also found that a minimal amount of media may be used to concentrate the microorganisms, enzymes, indicator material, and/or substrate molecules, which increases the signal while maintaining an increased path-length for the light.

The sterilization indicator may be configured to be activated by causing the breakable barrier to be opened. In one aspect, the container is configured for causing the breakable barrier to be opened. The cap is mountable on the container and may be mounted on the container in a first, non-activated position in which the breakable barrier is not opened and the growth medium remains in the cap. The container may include a projection or member adapted for opening the breakable barrier, and the cap may be moveable to a second, activated position in which the projection on the container causes the breakable barrier to be opened and release the growth medium into the container.

In another aspect, the breakable barrier may be openable by providing the breakable barrier as a self-breakable configuration. The breakable barrier may be self-breakable by being formed from a polymeric material that melts at a selected temperature. Additionally, a self-breakable barrier may be provided as a heat shrinkable film.

The sterilization indicator may be provided with a support member or members.

The base of the sterilization indicator may be configured to key the indicator to a holder, reader, incubator, or the like such that the indicator is designed to enter or be held in a holder, reader, incubator, or the like in a desired position.

In still another aspect, the present invention provides a method of assessing the efficiency of sterilization comprising: providing a self-contained sterilization indicator comprising (a) a container comprising a top, a bottom, an opening at the top, and defining an interior region; and (b) a cap having an inner chamber containing a growth medium, the inner chamber defining an opening adjacent the bottom of the cap and chamber, the cap further comprising a breakable barrier overlying the chamber; inoculating the container with microorganisms having a high sterilization resistance; mounting the cap on the container in a first position such that the breakable barrier is unbroken; subjecting the microorganisms to a sterilization process; causing the breakable barrier of the cap to break such that the growth media flows into the interior region of the container and contacts the microorganisms; incubating the microorganisms and the growth medium under conditions sufficient to promote the growth of microorganisms; and detecting the presence of viable microorganisms.

In still a further aspect, the present invention provides a biological indicator system comprising: a container having a lower, closed end, an upper end, and an opening at the upper end; a concentration of microorganisms disposed within the container; a cap mounted on the container over the upper end of the container, the cap having an upper, closed end, a lower, open end, an outer wall, an inner wall defining an inner chamber having an open end, a frangible barrier covering the open end of the inner chamber; and a liquid growth medium disposed within the inner chamber of the cap.

These and other features of the invention are described in reference to the following detailed description and the drawings.

BRIEF DESCRIPTION OF THE DRAWINGS

In the annexed drawings like parts and features have like references. A number of the annexed drawings are schematic illustrations, and which are not necessarily proportioned accurately or drawn to scale.

DETAILED DESCRIPTION

Figure 1:
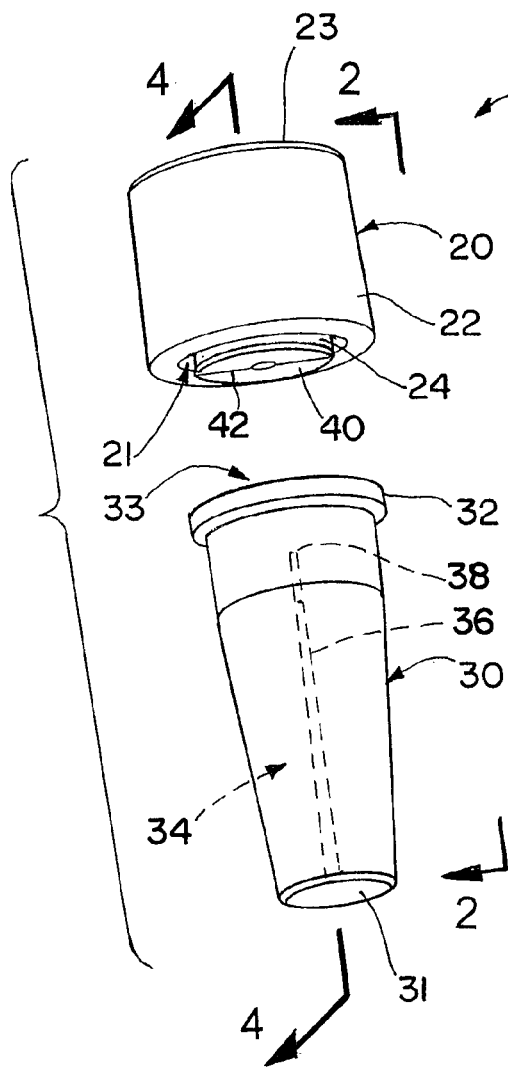
FIG. 1 is a perspective view of an exemplary self-contained sterilization indicator in accordance with an embodiment of the present invention showing the cap detached from the container.

All ranges and ratio limits disclosed in the specification and claims may be combined in any manner. It is to be understood that unless specifically stated otherwise, references to "a", "an", and/or "the" may include one or more than one, and that reference to an item in the singular may also include the item in the plural. All combinations specified in the claims may be combined in any manner.

The term "sterilization" refers to rendering a substance incapable of reproduction, metabolism, and/or growth. While this is often taken to mean total absence of living organisms, the term may be used herein to refer to a substance free from living organisms to a degree previously agreed to be acceptable. Unless otherwise indicated, the term "sterilization" may be used herein to also refer to processes less rigorous than sterilization, for example, disinfection, sanitization, decontamination, cleaning, and the like. Similarly, variations of the term "sterilization," such as sterilant, sterilizing, cleaning, sanitizing, etc., may also be used herein to refer to and encompass related variants associated with processes less rigorous than sterilization (e.g., disinfectant, disinfecting, etc.)

Generally, the present invention provides a self-contained sterilization indicator system suitable for evaluating a sterilization process comprising a cap adapted for housing a culture medium (also referred to herein as a growth medium) and a container adapted for housing microorganisms. The cap includes an inner chamber for housing the growth media and a breakable barrier (which may also be referred to as a frangible barrier) covering the inner chamber and encapsulating the growth medium in the chamber. The media-filled cap is mountable on the container, and the system is adapted for breaking the breakable barrier at a selected time so that the growth medium flows into the container containing the microorganisms. In one embodiment, the container may be adapted to break the breakable barrier. In another embodiment, the breakable barrier may be configured to break itself upon exposure to certain conditions.

Referring now to the drawings, FIGS. 1-4 show a sterilization indicator system 10 in accordance with a first exemplary embodiment of the present invention. The indicator system 10 comprises a cap 20 that is mountable on a container 30. The container 30 includes a closed, bottom end 31 and an open, upper end 33, and defines an interior space 34. The cap 20 has an outer wall 22, an open, lower end 21, and a closed, upper end 23. The cap also includes an inner wall (or walls) 24 disposed interior of the cap's outer wall and defining an inner chamber 26. The inner chamber 26 includes an opening 25 adjacent to the bottom end of the wall(s) 24. The chamber 26 contains a fluid 50, and the cap 20 includes a breakable barrier 40 disposed about the opening 25 of the chamber 26 to encapsulate the fluid 50 within the chamber 26.

Figure 2:
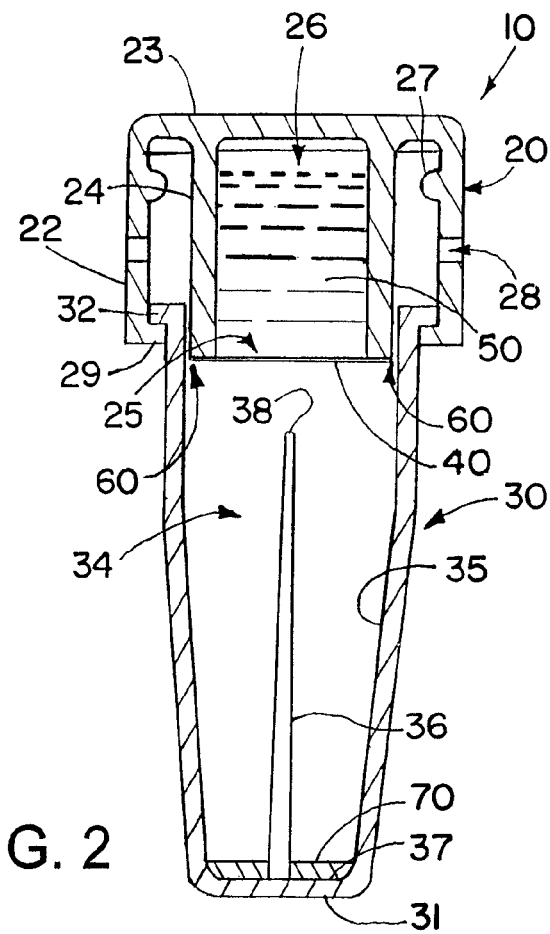
FIG. 2 is a cross-sectional view of the indicator of FIG. 1 (taken along line 2-2) showing the cap mounted on the container in a first non-activated position.
Figure 3:
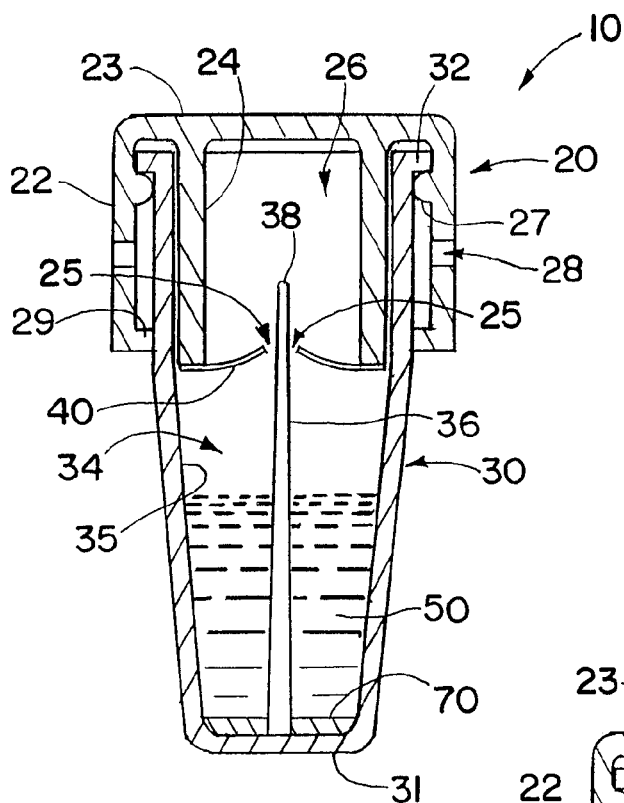
FIG. 3 illustrates the indicator as viewed in FIG. 2 with the cap mounted on the container in a second/activated position.
Figure 4:
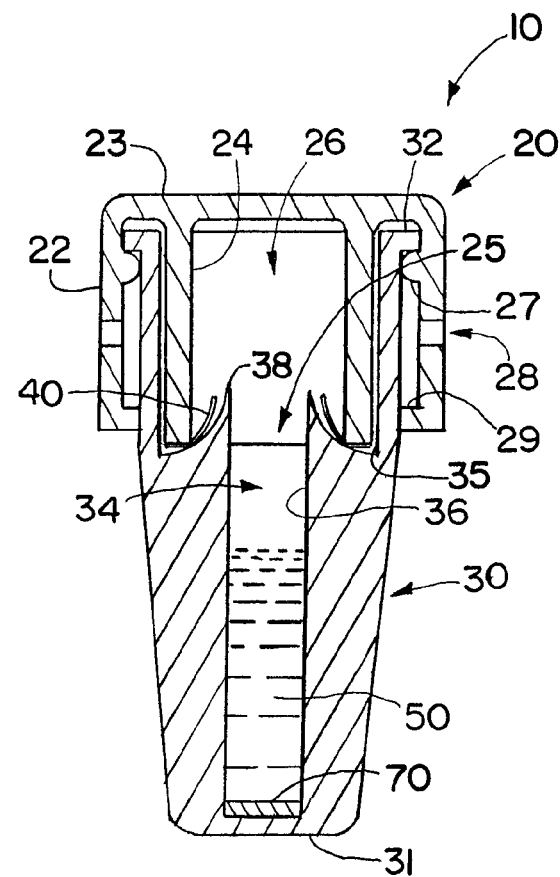
FIG. 4 is a cross-sectional view of the indicator of FIG. 3 rotated by 90°.

In the embodiment illustrated in FIGS. 1-4, the indicator system is configured for the cap 20 to be mounted to the container 30 in a snap-fit relationship. As shown in FIGS. 2-4, the container 30 includes an annular projection 32 forming a ridge or lip adjacent or near the upper end 33 of the container. The cap 20 includes an annular projection 29 forming a ridge or lip adjacent the bottom of the cap. The cap 20 may be mounted onto the container 30 by sliding the ridge 29 of the cap over the ridge 32 of the container. The ridge 32 of the container 30 engages the ridge 29 on the cap 20 to prevent the cap 20 and container 30 from decoupling. The cap 20 and container 30 may be sized such that the ridge 32 exerts a sufficient amount of pressure against the cap 20 to prevent the cap 20 from sliding downward without applying an external downward force to the cap 20. In this way, the breakable barrier 40 may be kept spaced apart from the edges 38 of puncture members 36 so the breakable barrier 40 does not contact and/or is not broken by the puncture members until such time as desired to activate the indicator.

As shown in FIGS. 1-4, the container 30 is adapted to break the breakable barrier 40. The containers include projections 36 (which may also be referred to herein as "puncture members") having edges 38 adapted to break or puncture the breakable barrier 40 when the breakable barrier 40 is moved downward toward and contacts the edge 38 of projection 36. The puncture members 36 are shown as being integral with and extending from the side wall 35 and the inner, bottom wall 37 of the container.

To evaluate a sterilization process, a calibrated concentration of microorganisms is disposed within the interior 34 of the container 30. The microorganisms may be disposed directly on the walls 35 of the container or may be provided on a support member (e.g., support member 70) that is disposed within the container 30. The indicator is then assembled by mounting the media filled cap 20 on the container 30. The cap 20 may be mounted by snap-fitting the cap 20 onto the container 30 as described above. With reference to FIG. 2, the media-filled cap 20 is mounted on the container 30 in a first, non-activated (or open) position such that the breakable barrier 40 is not punctured by the puncture members 36. Desirably, in the first, non-activated position, the breakable barrier 40 is positioned away from and does not contact the edges 38 of the puncture members 36.

With the indicator 10 being assembled such as shown in FIG. 2, the indicator may then be subjected to a sterilization process. The cap 20 is shown as having apertures 28 through which a sterilant vapor may enter and flow into indicator system. The sterilant enters the cap through apertures 28 (into the space between the outer wall 22 and the inner wall 24) and flows into container 30 through a space 60 defined between the exterior surface of inner wall 24 on the cap 20 and the inner surface of wall 35 on the container 30. The sterilant vapor flows into the container 30 and acts upon the microorganisms.

After the sterilization process is completed, the indicator may be activated by moving the cap 20 downward toward the container 30 to a second (or closed or activated) position, which is illustrated in FIGS. 3 and 4. The cap 20 is moved downward by applying a sufficient downward force or pressure on the cap 20. As the cap 20 is moved downward, the breakable barrier 40 is brought into contact with the edges 38 of the puncture members 36, and eventually moved into a position such that the edges 38 of puncture members 36 puncture or penetrate the breakable barrier 40. When the breakable barrier 40 is punctured, the opening 25 of the chamber 26 is exposed, and the liquid growth medium 50 drains into the interior region 34 of the container 30 and into contact with the microorganisms. It may be desirable to move the cap 20 downward with a twisting motion to effect a greater or maximum opening of the breakable barrier 40 to ensure complete drainage of the growth medium into the container.

As shown in FIGS. 3 and 4, the inner surface of the cap 20 includes a second annular projection 27, and the cap may be moved downward to a position such that the upper portion of the projection 27 engages the bottom of ridge 32 on the container 30, and the cap 20 is held in the second, closed/activated position. The second, closed/activated position may serve to hold the cap 20 in a sealed relationship with the container 30, which may prevent additional microorganisms from entering the system. The indicator 10 is then incubated for a sufficient period of time to allow microorganism viability to be determined. During incubation, any viable microorganisms will metabolize and grow, and this metabolism and growth releases byproducts into the culture medium. The byproducts may be detected by any selected property including, for example, pH change, color change, opacity, fluorescence, and the like.

It will be appreciated that the cap 20 need not include the second projection 27 to maintain the container in the closed position. In one alternative embodiment, the container 30 may include another annular projection or a set of detents (not shown) on the outside of the container 30 and located below the ridge 32, which projection or detents may be adapted to engage the ridge 29 on the cap to maintain the container 30 in a closed position. U.S. Pat. No. 5,770,393 illustrates such a configuration. In another alternative embodiment, the inner surface of the cap 20 and the outer surface of the container 30 may be threaded, and the cap 20 may be moved into and maintained in a closed position by screwing the cap 20 onto the container 30.

A second exemplary embodiment of a biological indicator system in accordance with the present invention is illustrated in FIGS. 6-10. A sterilization indicator 100 includes a media-filled cap 110 and a container 120. The media-filled cap 110 has an outer wall 112, a lower, open end 111, and a closed, upper end 113. The cap 110 includes an inner chamber 116 defined by an inner wall 114 that is spaced apart from the outer wall 112. The chamber 116 defines an opening 115 at the bottom of the inner wall 114. The inner chamber 116 is adapted for housing a fluid 140, and the cap includes a breakable barrier 130 disposed about the opening 115 to encapsulate the fluid within the chamber 116.

The container 120 has a closed, bottom end 121, an upper, open end 122, a wall 123, and defines an interior region 124. The container 120 includes puncture members 127 having an edge 128 suitable for puncturing and/or tearing the breakable barrier 130.

The cap 110 and container 120 are adapted for the cap 110 to be mounted to the container 120 in both a snap-fit and screw thread engagement. The cap 110 includes an annular projection 117 adapted to slide over projections 126 on the container 120 to engage the cap 110 with the container 120. The cap 110 also includes a threaded surface on the interior surface of wall 112 defined by projections 117 and recesses 119. The threaded surface may engage the projections 126 (which may serve as thread projections) on the container 120 in a screw-thread relationship, and the cap 110 may be moved into a fully closed position by screwing the cap 110 onto the container 120. It will be appreciated that screw thread assemblies do not have to have a snap-fit configuration.

Figure 7:
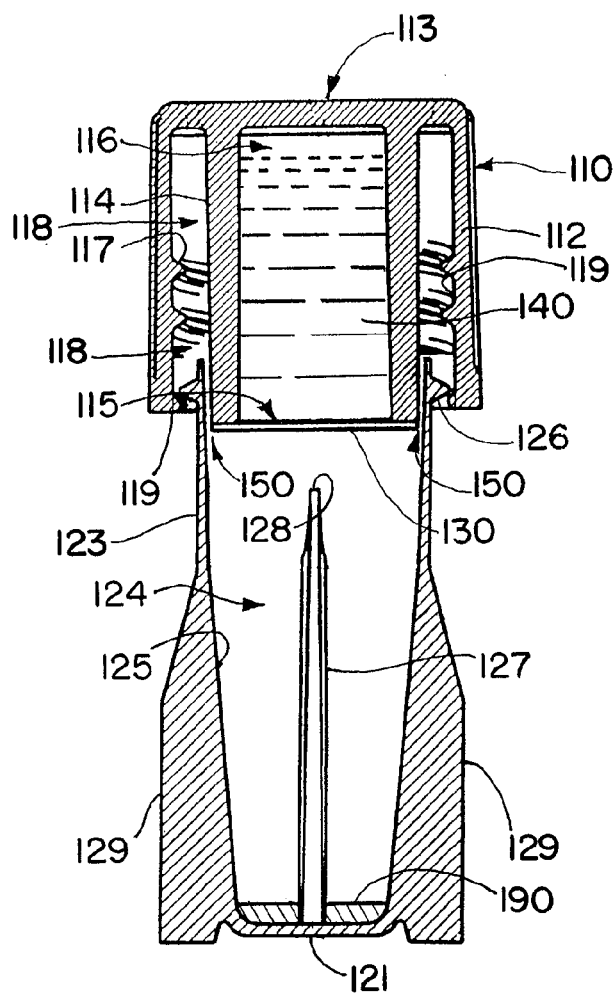
FIG. 7 is a cross-sectional view of the indicator of FIG. 6 (taken along the line 7-7) showing the cap mounted on the container in a first non-activated position.

The indicator 100 may be used in a manner similar to that described with respect to the previously described indicator 10. Microorganisms may be placed within the interior 124 of the container 120, for example, on a pad 190 and the cap 110 may be mounted on the container 120. As shown in FIG. 7, the cap 110 is mounted on the container 120 in a first, open (non-activated) position by sliding the projections 117 of the cap 110 over the projections 126 of the container 120 such that the projections 126 engage the projections 117 and hold the cap 110 in place.

The indicator 100 may then be subjected to a sterilization process. The sterilization vapor enters the cap 110 near the lower end of the cap 110 through a space between the cap 110 and the container 120. For example, in the embodiment depicted in FIGS. 6-10, the projections 126 are discontinuous such that there may be a space or opening between the outer surface of the container 120 and the inner surface of wall 112. The sterilent passes through this space/opening and enters into space 118 formed between wall 112 and wall 114. The sterilent passes over and around the projections 117 and over the open end 122 of the container 120 and flows into the container through a passageway 150 defined by a space between the inner surface of wall 125 of the container and the outer surface of wall 114 on the cap 110, and then acts upon the microorganisms.

Figure 8:
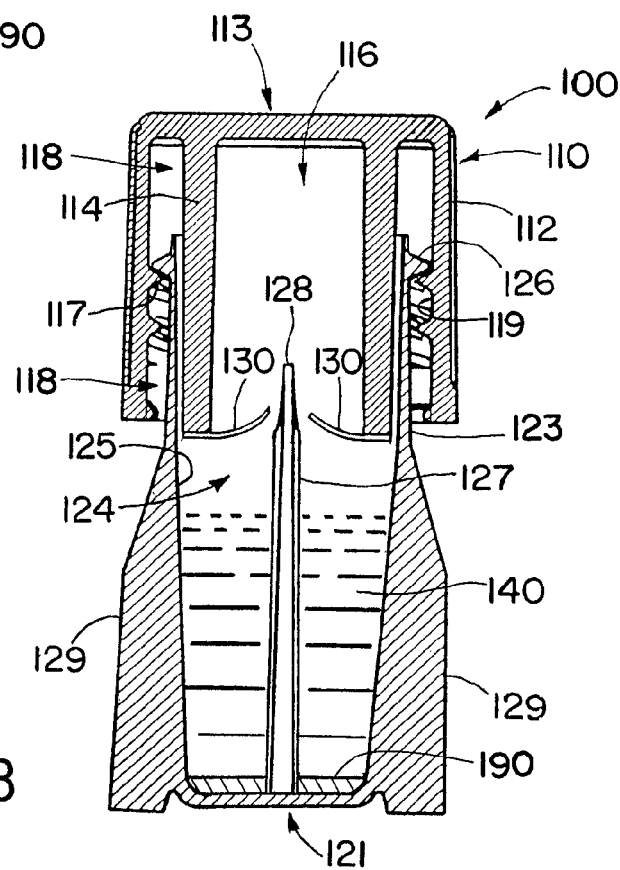
FIG. 8 is a cross-sectional view of the indicator of FIG. 6 (taken along the line 7-7) showing the cap mounted on the container in a second/activated position.
Figure 9:
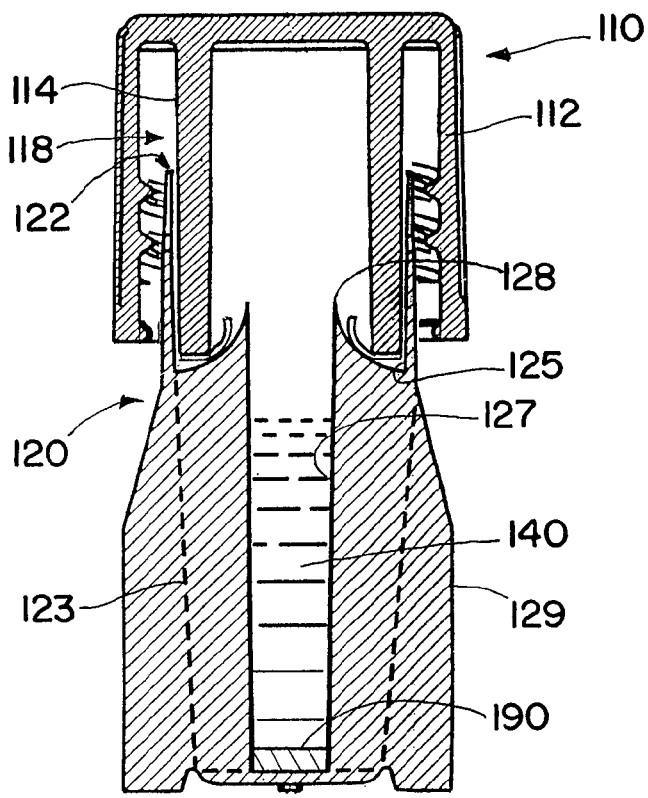
FIG. 9 is a cross-sectional view of the indicator of FIG. 6 (taken along line 9-9) showing the indicator in a second/activated position.

After the sterilization process, the indicator 100 is activated by moving the cap 110 into a second, closed position (FIGS. 8-9) by screwing the cap 110 onto the container 120. Screwing the cap 110 onto the container 120 causes the edges 128 of puncture members 127 to penetrate the breakable barrier 130, which causes the fluid 140 to drain from the inner chamber 116 of the cap 110 down into the container 120 and into contact with the microorganisms. As shown in FIGS. 8 and 9, the cap 110 may be moved to a position such that the uppermost thread engages the projections 126 to hold the cap 110 in a sealed relationship with the container to prevent additional microorganisms from entering the system and to provide a tortuous path for the passage of the sterilization medium. The indicator 100 may then be incubated for a sufficient period of time to determine microorganism viability.

Generally the cap (e.g., cap 20 or cap 110) may have any configuration, shape, and/or size as desired. Additionally, the configuration, including the shape and/or volume of the inner chamber (e.g., chambers 26 and 116) is not limited and may be selected as desired.

As described above, the cap 20 in the embodiment illustrated in FIGS. 1-4 is shown as having apertures 28 to allow for the ingress of the vapor sterilant into the indicator. It will be appreciated, however, that a cap need not be provided with such a feature. The number, size, shape, and/or location of the aperture(s) may be selected as desired. For example, the location, shape, and size of the apertures in the cap and/or the container may be selected to provide a tortuous path for the entrance and exit of the sterilization vapor between the microorganisms and the surrounding environments. The tortuous path may also serve to discourage contamination from external agents.

Apertures may be provided in the container in addition to or as an alternative to providing apertures in the cap. If apertures are not provided in the cap, the inner wall(s) need not be located to provide a space between the inner wall of the cap and the inner surface of the container. Additionally, if apertures are provided in the container, they should be located such that the growth medium does not leak or spill out through such apertures when the indicator is activated and the barrier is broken.

The container (e.g., containers 30 or 120) may be sized and shaped as desired to suit a particular purpose. As shown in the illustrated embodiments, the containers 30 and 120 have a generally conical shape where the side wall tapers toward the bottom of the container. That is, the side wall is substantially circular in cross section such that a cross sectional cut nearer the base is of a smaller diameter than a cross sectional cut further away from the base. Additionally, the geometry of the container's interior may be selected as desired for a particular purpose or intended use. Generally, the interior region is defined by the space between the conical side wall. The interior region may be made smaller by increasing the thickness of the sidewalls. The geometry of the container may generally be designed to serve as the light path for various detection methods such as spectroscopic detection methods. Desirably, the light path runs through the container. By providing the container with an interior having a relatively small volume (e.g., tapered geometry in the illustrated embodiments), a smaller volume of growth media is used to concentrate the organisms, metabolites (e.g., enzymes), indicators, and/or substrate molecules. This increases the signal while maintaining an increased path length for the light source.

Figure 10:
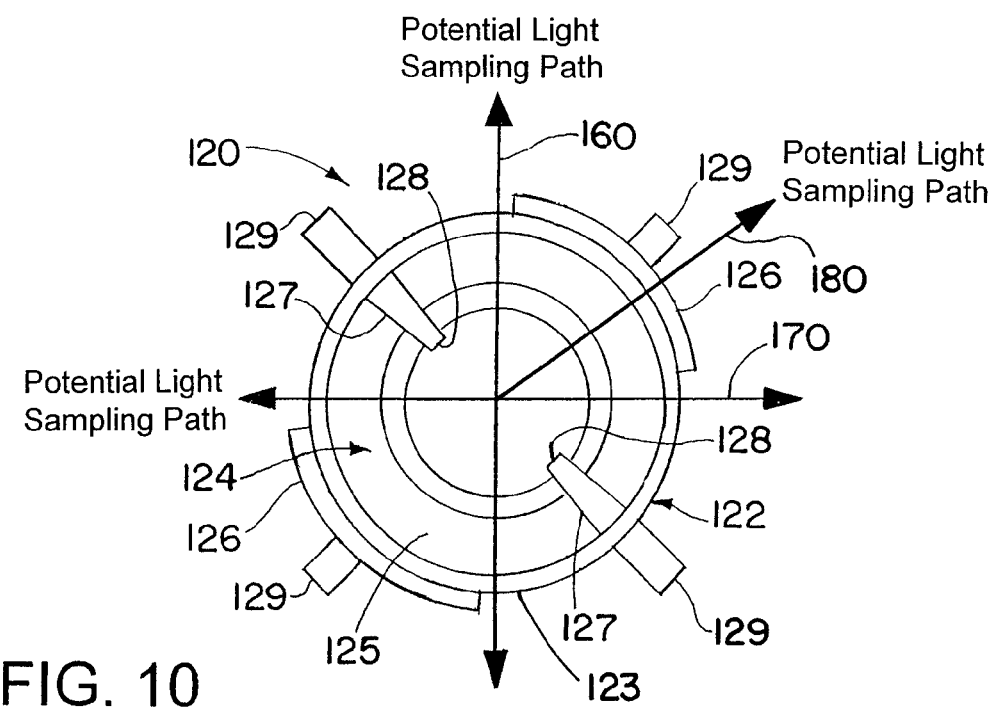
FIG. 10 is a top view of the indicator of the container of FIG. 6 with the cap removed and looking into the container.

It is also desirable for the light path to be substantially free of any objects that may interfere with the light from the light source. Thus, with an indicator system employing puncture members configured as shown in containers 30 and 120, the container would desirably be oriented in a detector such that the puncture members do not obstruct or interfere with the light path. Arrows 160, 170, and 180 in FIG. 10 illustrate potential light sampling paths for analyzing the indicator systems 10 and 100 spectroscopically. It will be appreciated that the light can be read (sighted) along any face of the container. The arrow 180 illustrates that a light source may be mounted in the bottom of the well of a reader.

The cap and container are configured for mounting the cap on the container. The mounting configuration is not particularly limited, and, as illustrated in indicator systems 10 and 100, the cap may be mounted to the container in a snap-fit and/or screw-thread relationship. As shown in indicator systems 10 and 100, a snap-fit configuration may be provided by providing projections on the cap and the container adapted for engaging one another. The design of such configurations is not limited. Similarly, there is no limitation regarding the design for an indicator system adapted for screw-thread mounting/closure. It will be appreciated that other mounting configurations are also contemplated. For example, an indicator system may be configured with an external latching mechanism or other mechanisms suitable for mounting the cap on the container and activating the indicator.

As shown in the illustrated embodiments, the container contains at least one puncture member (e.g., puncture members 36 and 127) adapted for penetrating or causing the breakable barrier to break when the indicator system is activated. The configuration, size, shape, location, and/or number of puncture members may be selected as desired. For example, while the illustrated embodiments are shown as having two puncture members that extend from the bottom of the container, it will be appreciated that one or more puncture members of similar or other configurations may be selected. As will be described later, the indicator system does not have to include a puncture member to break the breakable barrier.

Rather, the breakable barrier may be configured for self-breaking at a selected time and/or under certain conditions.

As shown in the embodiment in FIGS. 6-10, a container 120 may be provided with a support member such as, for example, legs 129. One or more support members may be provided to provide a self-supportive structure and/or to improve the stability of the indicator. Support members may also provide additional contacting surface for improved heat exchange with a heated surface (e.g., within a sterilization apparatus or with the incubator feature of a detector such as a fluorometer).

Figure 11:
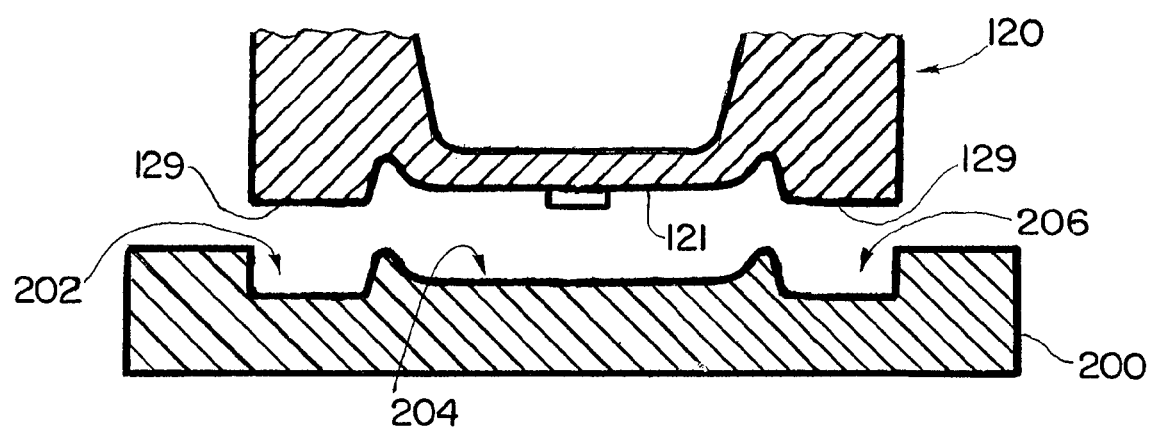
FIG. 11 illustrates the bottom of the indicator system in FIGS. 6-10 adapted for fitting into a reader or holder.

The underside of the container may be provided with a surface geometry suitable for keying the indicator system to a holder for placement in a particular sterilization apparatus, reader, incubator, etc., so that the container can enter a selected holder, reader, incubator, etc. and/or enter the holder, reader, incubator, etc. in a proper orientation. For example, while the legs 129 on the container 120 in FIGS. 6-10 may serve as support members to stabilize and/or support the container, they may also help define a surface geometry along the bottom and sides of the container 120. A holder, reader, incubator, or the like may be provided with a surface having grooves that correspond to the surface geometry/design of the bottom or sides of the container. For example, with reference to FIG. 11, a base 200, such as in a sterilizer, a reader, an incubator, a holder, or the like, may include depressions or grooves 202, 204, and 206, sized and shaped to receive a corresponding feature, such as the base of the legs 129 and bottom 121 of the container 120. Providing the base and sidewalls of the indicator system with a particular geometry keyed for receipt in a particular holder of a reader, detector, incubator, etc., may be desirable to ensure that the indictor enters into and is positioned within the reader/detector so that the container is positioned in the reader in an appropriate orientation. For example, with reference to FIG. 10, it may be desirable for the indicator system 100 to be placed in a reader or detector in a particular orientation to ensure that the container is oriented to provide an appropriate light path for the sample to be read. An indicator system could also be keyed to a particular incubator that is set to or sets itself to an appropriate temperature for the biological organism being used, as different organisms often require different temperatures for optimal growth.

It will be appreciated that the container does not have to have legs 129 to provide the container with a particular surface geometry suitable for keying the indicator to a holder. For example, the base of a container, such as the base of bottom end 31 of container 30 in FIGS. 1-4, could be provided with a pattern of grooves, depressions, projections, and the like to provide a particular surface geometry.

The cap and the container may be made from any material that is able to withstand the temperature and/or chemicals employed in a particular sterilization process. Different sterilization techniques may have different material requirements, and the material employed may be selected to suit a particular purpose or intended use. The cap and/or the container may be made, for example, from a polymeric material. Suitable polymeric materials include, but are not limited to, polyolefins, polystyrenes, polycarbonates, polymethacrylates, polyimides, polyesters, combinations of two or more thereof, and the like. Examples of suitable polyolefins include polyethylene, polypropylene, and the like. An exemplary material for the cap and/or the container is polypropylene, which is compatible with a variety of sterilants including hydrogen peroxide, steam, ethylene oxide, and peracetic acid. The container and the cap may be manufactured from the same material or they may be manufactured from different materials. To be suitable for use with methods for detecting the change in a property of the indicator, the container desirably has some transparency. For example, for fluorometric and spectroscopic detection methods, the container desirably has some transparency to the wavelength(s) of interest. If desired, the cap and/or the container may be colored.

The cap and/or container may be formed by any suitable method such as, for example, by molding methods as are known in the art. The breakable barrier may be configured as desired and made from any suitable material such that the barrier is capable of being broken to release the fluid from the cap into the container. As used herein, a breakable barrier is not limited to a structure that must be broken such as by puncturing the barrier with another object (e.g., by puncturing barriers 40 or 130 with the sharp edges of puncture members 36 or 127, respectively). The term "breakable barrier" may also encompass a barrier that is "self-breakable" and as a result of a physical property or change in physical property under certain conditions.

In one embodiment, such as in the embodiments illustrated in FIGS. 1-10, the breakable barrier is constructed as a barrier layer that is to be broken by another object (e.g., puncture members) penetrating through the barrier. Such a barrier layer may be formed from a polymeric material, a metal foil, or a combination of two or more thereof. Suitable polymeric materials include polyolefins, polystyrenes, polymethacrylates, polyimides, polyacrylamides, combinations of two or more thereof, and the like. An exemplary polymeric material for the breakable barrier is a biaxially oriented polyester. An exemplary metal foil/polymer combination for the breakable barrier is Alcon DD225, which is a metal foil with a lacquered side and a polypropylene coated side.

Figure 5:
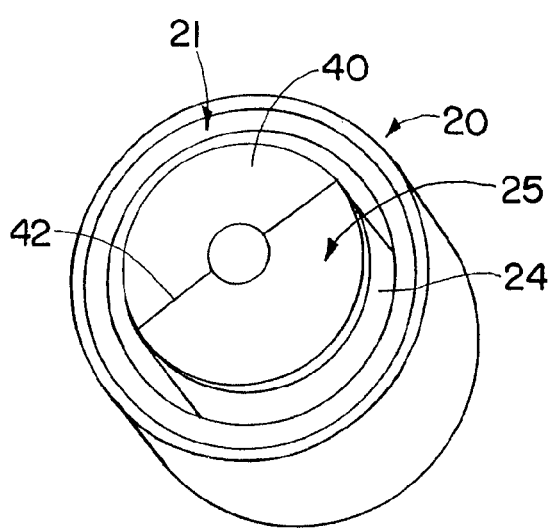
FIG. 5 is a bottom perspective view of the cap from the indicator of FIG. 1.
Figure 6:
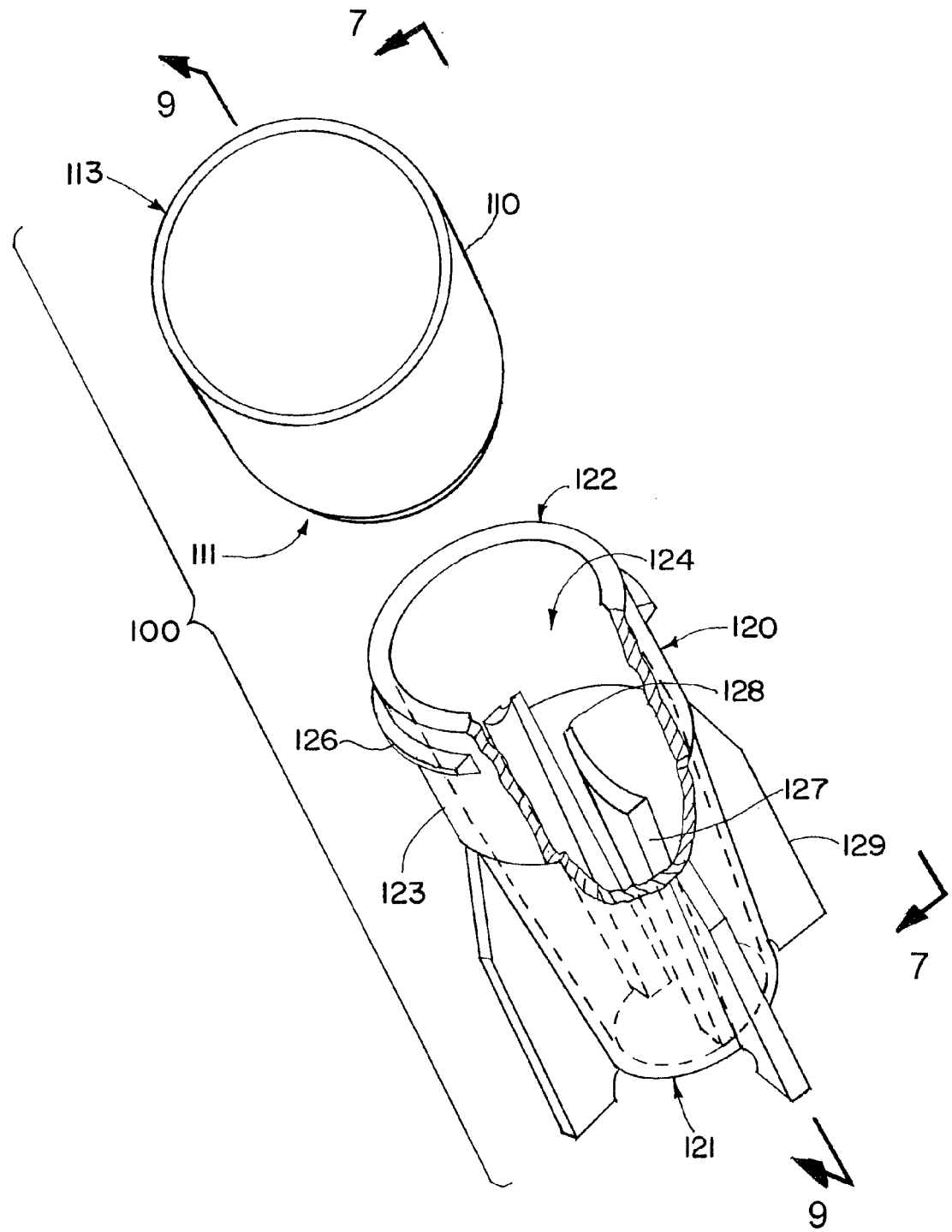
FIG. 6 is a perspective view of an exemplary self-contained sterilization indicator in accordance with another embodiment of the present invention showing the cap detached from the container.

The barrier may be provided as a film and may have any thickness as desired provided the film is capable of being broken by the puncture members when the cap is moved into a closed position. In one embodiment, the breakable barrier has a thickness in the range of from about 0.5 to about 10 mils. In another embodiment, the breakable barrier has a thickness in the range of from about 0.5 to about 2.5 mils. The breakable barrier may be formed as a single layer construction or a multi-layer construction. The breakable barrier may be designed to facilitate puncturing of the barrier by the puncture members. For example, the barrier layer may be provided with an area of weakness to aid in effectively puncturing the barrier. Areas of weakness may be provided, for example, by providing the barrier with one or more areas that are thinner and easier to puncture (i.e., require less force to puncture) relative to the remainder of the barrier layer. Areas of weakness may also be provided by providing the film with a score line, die-cut line, perforated line, or the like. As shown in FIGS. 1 and 5, the film 40 includes a die-cut line 42.

In another embodiment, the breakable barrier may be self-breakable and be formed from a material that undergoes a physical change upon heating, which physical change results in the barrier being broken. For example, in one embodiment, the barrier may be formed from a polymeric material having a selected melting point such that the indicator is activated by heating the indicator (at a selected temperature) thereby causing the barrier to break by melting and releasing the growth medium into the container. In another embodiment, the barrier layer may be formed from a heat shrinkable film having suitable properties to facilitate breakage of the film upon exposure to a selected temperature. For example, the film may be a heat shrinkable film having a relatively low tear strength such that the film tears upon shrinking thereby releasing the growth medium into the container. The materials for a barrier that break by melting or tearing (due to shrinking) are ascertainable by persons skilled in the art and may be selected based upon the particular sterilization method being employed and/or the desired conditions to activate the indicator. Heat shrinkable films typically include oriented films, such as, for example, oriented polypropylene films. In one embodiment, the barrier may be adapted to break at or around the sterilization temperature (provided the indicator is exposed to the sterilization process for a sufficient period of time before the barrier is broken). In another embodiment, it may be desirable for the barrier to not undergo the self-breakable physical change (e.g., melting, shrinking, and/or tearing) until after the indicator system has been exposed to the sterilization conditions for a sufficient period of time. That is, it may be desirable for the barrier to not undergo the desired change in physical property at the sterilization temperatures, but to exhibit the change at a temperature greater than the sterilization temperature. In this instance, the indicator system may be exposed to the sterilization conditions at a first temperature for a selected period of time, and then exposed to a second temperature (greater than the sterilization temperature) to cause the barrier to break (such as by melting or shrinking or tearing). The self-breaking barrier may be particularly suitable for use in steam or dry heat sterilization processes.

The cap and container may be formed by any suitable method for forming the desired shape and/or configurations. Caps and containers formed from polymeric materials may be formed by various molding methods such as, for example, injection molding.

The media filled cap may be provided by providing a cap structure having an inner chamber suitable for containing the liquid media. The inner chamber may then be filled with a selected growth medium, and a breakable barrier may be attached to the inner chamber so as to cover the access opening of the chamber and encapsulate the growth medium within the inner chamber. The breakable barrier may be attached to the chamber by any suitable method including, for example, by an adhesive, sonic welding, heat sealing, and the like. The breakable barrier may have one or both sides corona treated, treated with an adhesive, coated with a lacquer or polymer film, or metalized to facilitate attachment of the film to the chamber. An exemplary barrier layer is a lacquered aluminum foil, which facilitates heat sealing to a variety of polymeric materials including polypropylene.

The test microorganism may be selected as desired based on the sterilization process being evaluated. Generally, the test microorganism should have a high resistance to the sterilization process being evaluated. Bacterial spores are exemplary microorganisms, because they generally have a high resistance to many different sterilization processes. Other suitable microorganisms include yeasts, fungi, and bacteria in the vegetative state. Exemplary bacterial spores include, for example, *Bacillus pumilus, Bacillus coagulans, Bacillus subtilis, Bacillus circulans, Bacillus atrophaeus, Geobacillus stearothermophilus, Deinococcus radiodurans, Aspergillus niger*, and the like. A single type of test microorganisms or combinations of test microorganisms may be used. The concentration of test microorganisms may be selected as desired for a particular purpose. In one embodiment, the concentration of test microorganisms may be in the range of from about $10^5$ to about $10^{10}$ colony forming units (cfu).

As previously described, the test microorganisms may be inoculated on the bottom or on the walls of the container. Alternatively, the microorganisms may be placed on a support, which is then disposed within the container. Any suitable support material may be used including, for example, a cellulose-based support, a glass fiber based support, or a polymeric support. A non-limiting example of a suitable support includes a spore inoculated element that is wrapped in or encapsulated in a microporous, hydrophilic membrane as disclosed in U.S. Pat. No. 5,516,648, which is incorporated herein by reference.

The growth medium may be selected as desired for a particular purpose or intended use. Examples of suitable growth media include aqueous solutions of soybean-casein digest broth, Dextrose Tryptone, and fluid thyoglycollate. An exemplary growth medium is Tryptic Soy Broth (TSB). In steam or dry heat applications, agar-based media may be used. Agar-based media are generally semi-solid at room temperature, and upon exposure to steam or dry heat, the agar melts. Upon activation of the indicator, the breakable barrier is broken and melted agar flows into the container that contains the test microorganisms and generally remains liquid at the temperatures used for monitoring.

The growth medium may comprise an indicator that undergoes a property change, which is capable of being detected and/or measured, in response to the growth of a particular microorganism. For example, the detector may be provided to react with a particular metabolite (e.g., an enzyme) produced by the growing microorganisms, which results in a color change, a pH change, a pH and a color change, a change in fluorescence (e.g., fluorescing or fluorescence), a change in turbidity, and the like. Desirably, the metabolite is selected such that relatively quick or early detection of microorganism activity is achieved. Desirably, the indicator is present in an amount sufficient to provide detectable quantities of the indicator, in the presence of the metabolite, within a period of about two hours (or less) following the completion of the sterilization process. The indicator may be selected based on the test microorganism being used and the metabolite of interest. Suitable metabolites and an appropriate indicator for detecting the metabolite are readily ascertainable by persons skilled in the art. A non-limiting example of a suitable metabolite of interest is an enzyme such as alpha amylase, which is secreted in bacterium such as *Bacillus subtilis*, proteases, and the like. Suitable indicators include, but are not limited to, biologically active molecules, fluorescent dyes, dyes, chromogenic substances, pigments, acids, bases, radio-labelled compounds, molecules that exhibit fluorescence, molecules that cease to fluoresce, and the like. An exemplary indicator is a fluorescent substrate such as, for example, 4-methylumbelliferyl-α-D-glucopyroside (MUD), 4-methylumbelliferyl-β-D-galactopyronoside (MUG), and the like.

The detection method may be selected based on the property of interest and may include, for example, fluorometric, visual, pH, and spectroscopic detection methods. The detection of a measurable change in an indicator property within an established period of time indicates viability of microorganisms and inadequate sterilization. The absence of a measurable change within the established period of time demonstrates that the sterilization process was lethal to the test microorganisms and, thus, adequate.

The growth medium may also contain a substance that reduces the toxicity of the growth medium toward the metabolite. Suitable toxicity reducing substances include, for example, activated charcoal, bovine serum albumin, a soluble starch, and the like.

While the method of using the sterilization indicator has been described with respect to biological indicators, it will be appreciated that the indicator is not so limited and may be used as an enzymatic indicator, a dual biological/enzymatic indicator, and the like. In one embodiment, the sterilization indicator may be used as an enzymatic indicator. In such an application, an active enzyme may be placed in the container, and a substrate that reacts with the enzyme may be placed in the inner chamber of the cap and sealed within the cap's inner chamber by the breakable barrier. The active enzyme may be impregnated on a carrier strip and disposed within the container. The indicator is then subjected to a sterilization process. The sterilant enters the container and contacts the active enzyme on the carrier strip. After the sterilization procedure, the indicator may be activated as previously described by moving the cap downward such that the breakable barrier is broken (e.g., by being punctured by the puncture member(s) within the container) and the substrate flows into the container where it can contact the enzyme on the carrier strip.

The effectiveness of the sterilization procedure may be evaluated by evaluating the activity of the enzyme. The enzyme and substrate are chosen such that the substrate reacts with the active enzyme to form a detectable product. Generally, the inactivation of the enzyme will be correlated with the death of test microorganisms in the indicator. The enzyme selected for use in a biological indicator should be at least as resistant (and desirably more resistant) to a sterilization procedure as microorganisms that are likely to be present as contaminants. The enzyme should remain sufficiently active to form a detectable enzyme-substrate product after a sterilization cycle that fails to kill contaminating microorganisms, yet be inactivated by a sterilization cycle that kills contaminating microorganisms. If the sterilization procedure works properly, the enzyme is inactivated during the procedure, and there is no detectable product. If the sterilization procedure does not work properly, the enzyme is not inactivated, and the enzyme will react with the substrate to form a detectable product. The enzyme-substrate product may be detectable as a color change, a fluorescent signal, a luminescent signal, or the like.

The enzyme and substrate are not limited and may be selected as desired for a particular purpose or intended use. A person skilled in the art will be able to ascertain and select an appropriate substrate that will react with an active enzyme to produce a product that is detectable by fluorescence, color change, and the like.

An active enzyme may be obtained from various sources such as (i) the purified, isolated enzyme derived from an appropriate microorganism, (ii) a microorganism to which the enzyme is indigenous or added by genetic engineering, or (iii) a microorganism to which the enzyme has been added during sporulation or growth such that the enzyme is incorporated or associated with the microorganism. Suitable enzymes include enzymes derived from spore-forming microorganisms, such as *Bacillus stearothermophilus* and *Bacillus subtilis*. Enzymes from spore-forming microorganisms that are useful in the biological indicators of the invention include, but are not limited to, β-D-glucosidase, α-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, α-D-galactosidase, β-D-galactosidase, tyrosine aminopeptidase, phenylalanine aminopeptidase, β-D-glucuronidase, α-L-arabinofuranosidase, N-acetyl-B-glucosaminodase, β-D-cellobiosidase, alanine aminopeptidase, proline aminopeptidase and a fatty acid esterase, derived from spore forming microorganisms.

Chromogenic and fluorogenic substrates that react with enzymes to form detectable products, and that are suitable for use in the sterilization indicator of the invention, are known in the art. Substrates may be classified in two groups based on the manner in which they create a visually detectable signal. The substrates in the first group react with enzymes to form enzyme-modified products that are themselves chromogenic or fluorescent. The substrates in the second group form enzyme-modified products that must react further with an additional compound to generate a color or fluorescent signal. A number of fluorogenic substrates for enzymes of diverse origin which are known, commercially available, and have been used in enzymological procedures. Among these are a variety of fluorogenic 4-methylumbelliferyl derivatives (hydrolysable to 4-methylumbelliferone); derivatives of 7-amido-4-methyl-coumarin; diacetylfluorescein derivatives; and fluorescamine.

Useful 4-methylumbelliferyl derivatives include, but are not limited to, 4-methylumbelliferyl-2-acetamido-4, 6-0-benzylidene-2-deoxy-β-D-glucopyranoside; 4-methylumbelliferyl acetate; 4-methylumbelliferyl-N-acetyl-β-D-galactosaminide; 4-methylumbelliferyl-N-acetyl-α-D-glucosaminide; 4-methylumbelliferyl-N-acetyl-β-D-glucosaminide; 2'-(4-methylumbelliferyl)-α-D-N-acetyl neuraminic acid; 4-methylumbelliferyl α-L-arabinofuranoside; 4-methylumbelliferyl-β-L-arabinoside; 4-methylumbelliferyl butyrate; 4-methylumbelliferyl β-D-cellobioside; methylumbelliferyl β-D-N, N'-diacetyl chitobioside; 4-methylumbelliferyl elaidate; 4-methylumbelliferyl β-D-fucoside; 4-methylumbelliferyl α-L-fucoside; 4-methylumbelliferyl β-L-fucoside; 4-methylumbelliferyl α-D-galactoside; 4-methylumbelliferyl β-D-galactoside; 4-methylumbelliferyl α-D-glucoside; 4-methylumbelliferyl β-D-glucoside; 4-methylumbelliferyl β-D-glucuronide; 4-methylumbelliferyl p-guanidinobenzoate; 4-methylumbelliferyl heptanoate; 4-methylumbelliferyl α-D-mannopyranoside; 4-methylumbelliferyl β-D-mannopyranoside; 4-methylumbelliferyl oleate; 4-methylumbelliferyl palmitate; 4-methylumbelliferyl phosphate; 4-methylumbelliteryl propionate; 4-methylumbelliferyl stearate; 4-methylumbelliferyl sulfate; 4-methylumbelliferyl β-D-N, N', N"-triacetyl-chitotriose; 4-methylumbelliferyl 2,3,5-tri-o-benzoyl-α-L-arabinofuranoside; 4-methylumbelliferyl-p-trimethylammonium cinnamate chloride; and 4-methylumbelliferyl β-D-xyloside.

The present invention may be further understood with reference to the following example. The examples are not intended to limit the invention in any manner but only to further illustrate various aspects of the invention.

EXAMPLES

A self-contained biological indicator is designed having a cap and container similar to that illustrated in FIGS. 6-10. The cap and the container are formed from polypropylene via a molding process. The cap is filled with 0.5 ml of a growth medium containing a fluorescent substrate. The growth medium has the following formulation:

| | |
|---|---|
| Pancreatic digest of casein: | 17 g |
| Enzymatic digest of soybean meal: | 3 g |
| Sodium chloride: | 5 g |
| Dipotassium phosphate: | 2.5 g |
| Dextrose: | 2.5 g |
| Distilled water: | 1 liter |

To the above growth medium is added 0.2 g of 4-mehtylumbelliferyl-β-D-galactopyronoside (MUG) as the fluorescent substrate. The inner chamber of the media filled cap is covered with a breakable barrier formed from a 1 mil thick lacquered aluminum foil. The cover film is secured to the inner chamber by heat sealing.

The bottom of the container is inoculated with $10^5$ or $10^6$ cfu (colony forming units) of *Geobacillus stearothermophilus*. The cap is mounted on the container and the sample is autoclaved. Following autoclaving, the indicator is activated by screwing the cap down with a force greater than or equal to about 4 lbs/in, which causes the breakable barrier to be broken by the puncture members. A control indicator containing $10^5$ or $10^6$ cfu of *Geobacillus stearothermophilus* is activated in a similar manner. The indicators are then incubated at 55-60° C. in an 8-well, 2-temperature fluorescence incubator/reader available from STERIS Corporation. The fluorescent reader excites the sample at 365±20 nm and detects the emission from the sample at 420±nm.

In yet another embodiment, $10^5$ or $10^6$ cfu of *Bacillus atrophaeus* is used in place of *Geobacillus stearothermophilus* for the evaluation of ethylene oxide based sterilization and the resulting activated indicator is incubated at 37° C. in the 8-well, 2-temperature fluorescent reader described above.

While the disclosed invention has been explained in relation to various detailed embodiments, it is to be understood that various modifications thereof may become apparent to those skilled in the art upon reading the specification. Therefore, it is to be understood that the invention specified herein is intended to include such modifications as may fall within the scope of the appended claims.

The invention claimed is:

1. A self-contained sterilization indicator for determining the effectiveness of a sterilization process, the sterilization indicator comprising:
   a polymeric container for holding a concentration of microorganisms and/or an enzyme, the container having an upper end, a lower end, and an opening at the upper end;
   a cap for holding a growth medium, the cap having an outer wall, an upper, closed end, a lower end, an opening adjacent the lower end of the cap, and a separately spaced inner wall defining an inner chamber having an opening adjacent the lower end of the cap, the inner chamber for holding a growth medium and/or a substrate reactive with the enzyme, the cap comprising a breakable barrier overlying and covering the opening of the inner chamber; and
   at least one projection disposed within the polymeric container for puncturing the breakable barrier covering the opening of the inner chamber of the cap.

2. The self-contained sterilization indicator according to claim 1, wherein the cap is mountable on the container in a first position in which the breakable barrier is separated from the edge of the at least one projection, and the cap is moveable to a second position in which the projection causes the breakable barrier to break thereby releasing a growth medium into the container.

3. The self-contained sterilization indicator of claim 1, wherein the cap and container are configured for mounting the cap on the container in a snap-fit relationship.

4. The self-contained sterilization indicator of claim 1, wherein the cap and container are configured for mounting the cap and the container in a screw-thread relationship.

5. The self-contained sterilization indicator of claim 1, wherein the cap and the container are independently formed from a polymeric material that is chosen from a polyolefin, a polystyrene, a poly(meth)acrylate, a polyester, a polyimide, a polyacrylamide, a polycarbonate, or a combination of two or more thereof.

6. The self-contained sterilization indicator according to claim 5, wherein the polymeric material comprises a polyolefin chosen from polyethylene, polypropylene, or a combination thereof.

7. The self-contained sterilization indictor according to claim 1, wherein the container further comprises at least two support members extending from the outer surface of the container.

8. The self-contained sterilization indicator according to claim 1, wherein at least one of the cap and/or the container comprises at least one aperture through which a sterilant enters into the container.

9. The self-contained sterilization indicator according to claim 1, wherein the breakable barrier is formed from a polymeric material, a metal foil, or a combination thereof.

10. The self-contained sterilization indicator according to claim 1, wherein the breakable barrier comprises a polymeric material chosen from a polyolefin, a polystyrene, a poly(meth)acrylate, a polyester, a polyimide, a polyacrylamide, a polycarbonate, or a combination of two or more thereof.

11. The self-contained sterilization indicator according to claim 10, wherein at least one side of the breakable barrier is corona treated.

12. The self-contained sterilization indicator according to claim 10, wherein at least one side of the breakable barrier is metallized.

13. The self-contained sterilization indicator according to claim 1, wherein the breakable barrier has a first thickness and at least one area having a second thickness that is less than the first thickness.

14. The self-contained sterilization indicator according to claim 1, wherein the breakable barrier comprises a die-cut line.

15. The self-contained sterilization indicator according to claim 1, wherein the breakable barrier is self-breakable and is breakable by melting.

16. The self-contained sterilization indicator according to claim 1, wherein the breakable barrier is formed from a heat shrinkable film.

17. The self-contained sterilization indicator according to claim 1, wherein the breakable barrier is attached to the chamber of the cap by an adhesive, a heat seal, sonic welding, or a combination of two or more thereof.

18. The self-contained sterilization indicator according to claim 1, wherein the indicator defines at least one tortuous path for entry of sterilant into the container.

19. A method of assessing the efficiency of sterilization comprising:
   (1) providing a self-contained biological indicator comprising
      (a) a polymeric container for holding a concentration of microorganisms, the container having an upper end, a lower end, and an opening at the upper end;
      (b) a cap for holding a growth medium for the microorganisms, the cap having an outer wall, an upper, closed end, a lower end, an opening adjacent the lower end of the cap, and a separately spaced inner wall defining an inner chamber having an opening adjacent the lower end of the cap, the inner chamber holding the growth medium, the cap comprising a breakable barrier overlying and covering the opening of the inner chamber; and
      (c) at least one projection disposed within the polymeric container for puncturing the breakable barrier covering the opening of the inner chamber of the cap;
   (2) inoculating the container with microorganisms having a high sterilization resistance;

(3) mounting the cap on the container in a first position such that the breakable barrier is unbroken;
(4) subjecting the microorganisms to a sterilization process;
(5) causing the breakable barrier of the cap to break such that the growth media flows from the inner chamber of the cap into the interior region of the container and contacts the microorganisms;
(6) incubating the microorganisms and the growth medium under conditions sufficient to promote the growth of microorganisms; and
(7) detecting the viability of the microorganisms.

20. The method according to claim 19, wherein the breakable barrier is broken by moving the cap from the first position to a second position in which the at least one projection causes the breakable barrier to break open.

21. The method according to claim 19, wherein the breakable barrier is formed from a meltable polymeric film, and the barrier is broken by exposing the self-contained biological indicator to a temperature sufficient to melt the barrier.

22. The method according to claim 21, wherein the growth medium comprises agar.

23. The method according to claim 19, wherein the breakable barrier is formed from a heat shrinkable polymeric film, and the barrier is broken by exposing the self-contained biological indicator to a temperature sufficient to cause the barrier to shrink and tear apart.

24. The method according to claim 23, wherein the growth medium comprises agar.

25. The method according to claim 19, wherein the microorganisms are disposed on an inner surface of the container.

26. The method according to claim 19, wherein the microorganisms are deposited on a substrate that is disposed in the interior region of the container.

27. The method according to claim 19, wherein the cap, the container, or both define at least one tortuous path for entry of the sterilant into the container.

28. A biological indicator system comprising:
a polymeric container having a lower, closed end, an upper end, and an opening at the upper end; a concentration of microorganisms disposed within the container;
a cap mounted on the container over the upper end of the container, the cap having an outer wall, an upper, closed end, a lower end, and a separately spaced inner wall defining an inner chamber having an opening adjacent the lower end of the cap, the inner chamber comprising a liquid growth medium sealed within the inner chamber by a frangible barrier covering the open end of the inner chamber of the cap; and
at least one projection disposed within the polymeric container for puncturing the fragile barrier covering the opening of the inner chamber of the cap.

29. The biological indicator system according to claim 28, the cap being mounted on the container for movement between a first position and a second position, wherein the frangible barrier is displaced from the puncture member in the first position and the puncture member punctures and tears the frangible barrier as the cap is moved from the first position to the second position.

30. The biological indicator system according to claim 28, wherein the frangible barrier comprises a polymeric material that undergoes a physical change upon exposure to an elevated temperature, the physical change causing the frangible barrier to break.

31. The biological indicator system according to claim 30, wherein the physical change is melting.

32. The biological indicator system according to claim 30, wherein the physical change is shrinking and/or tearing.

33. The biological indicator system according to claim 28, wherein at least one of the cap and/or the container comprises at least one aperture for receiving a sterilization fluid.

34. The biological indicator system according to claim 33, wherein the cap comprises at least one aperture and the cap cooperates with the container to admit the sterilant fluid into the container.

35. The biological indicator system according to claim 28, wherein the lower end of the container defines a base with an outer surface, and the outer surface of the base defines a surface geometry, the surface geometry providing a keyed pattern, which may be fitted together to a corresponding pattern of an apparatus for holding the biological indicator system.

36. The biological indicator system according to claim 28, further comprising at least one support member extending from the exterior surface of the container.

37. The biological indicator system according to claim 36, wherein the lower end of the container defines a base surface, and the base surface and at least one support member define a base surface geometry providing a keyed pattern, which may be fitted together to a corresponding pattern of a surface of an apparatus for holding the biological indicator system.

38. A method of assessing the efficiency of sterilization comprising:
(1) providing a self-contained sterilization indicator comprising:
(a) a polymeric container comprising a top, a bottom, an opening at the top, and defining an interior region;
(b) a cap having an outer wall, an upper, closed end, a lower end, an opening adjacent the lower end of the cap and a separately spaced inner wall defining an inner chamber containing a solution comprising a substrate reactive with an active enzyme, the cap further comprising a breakable barrier overlying the chamber; and
(c) at least one projection disposed within the polymeric container for puncturing the breakable barrier;
(2) disposing a concentration of active enzymes within the container, the enzymes having a high sterilization resistance;
(3) mounting the cap on the container in a first position such that the breakable barrier is unbroken;
(4) subjecting the enzymes to a sterilization process;
(5) causing the breakable barrier of the cap to break by said at least one projection such that the solution comprising the substrate flows into the interior region of the container and contacts the enzymes; and
(6) detecting the activity of the enzymes.

* * * * *